(12) United States Patent
Cappola et al.

(10) Patent No.: US 8,336,754 B2
(45) Date of Patent: Dec. 25, 2012

(54) LOCKING ARTICULATION MECHANISM FOR SURGICAL STAPLER

(75) Inventors: Kenneth M. Cappola, Monroe, CT (US); Paul Scirica, Huntington, CT (US); Patrick Mozdzierz, Glastonbury, CT (US); Frank Marini, Monroe, CT (US)

(73) Assignee: Covidien LP, Mansfield, MA (US)

( * ) Notice: Subject to any disclaimer, the term of this patent is extended or adjusted under 35 U.S.C. 154(b) by 34 days.

(21) Appl. No.: 13/021,023

(22) Filed: Feb. 4, 2011

(65) Prior Publication Data
US 2012/0199629 A1    Aug. 9, 2012

(51) Int. Cl.
*A61B 17/068* (2006.01)

(52) U.S. Cl. ............... 227/178.1; 227/175.2; 227/19

(58) Field of Classification Search ............... 227/178.1, 227/175.2, 19
See application file for complete search history.

(56) References Cited

U.S. PATENT DOCUMENTS

| | | | | |
|---|---|---|---|---|
| 4,869,414 A | * | 9/1989 | Green et al. | ............ 227/19 |
| 5,312,023 A | * | 5/1994 | Green et al. | ............ 227/175.1 |
| 5,330,502 A | | 7/1994 | Hassler et al. | |
| 5,397,046 A | | 3/1995 | Savage et al. | |
| 5,482,197 A | | 1/1996 | Green et al. | |
| 5,485,952 A | * | 1/1996 | Fontayne | ............ 227/178.1 |
| 5,575,799 A | | 11/1996 | Bolanos et al. | |
| 5,577,654 A | | 11/1996 | Bishop | |
| 5,584,425 A | | 12/1996 | Savage et al. | |
| 5,588,580 A | | 12/1996 | Paul et al. | |
| 5,588,581 A | | 12/1996 | Conlon et al. | |
| 5,626,587 A | | 5/1997 | Bishop et al. | |
| 5,673,840 A | | 10/1997 | Schulze et al. | |
| 5,673,841 A | | 10/1997 | Schulze et al. | |
| 5,702,408 A | | 12/1997 | Wales et al. | |
| 5,704,534 A | | 1/1998 | Huitema et al. | |
| 5,713,505 A | | 2/1998 | Huitema | |
| 5,762,255 A | * | 6/1998 | Chrisman et al. | ............ 227/175.2 |
| 5,820,009 A | * | 10/1998 | Melling et al. | ............ 227/176.1 |
| 5,823,066 A | | 10/1998 | Huitema et al. | |
| 5,855,311 A | | 1/1999 | Hamblin et al. | |
| 5,862,715 A | | 1/1999 | Lemire | |
| 5,901,895 A | | 5/1999 | Heaton et al. | |
| 6,716,232 B1 | | 4/2004 | Vidal et al. | |
| 6,786,382 B1 | * | 9/2004 | Hoffman | ............ 227/178.1 |
| 6,964,363 B2 | | 11/2005 | Wales et al. | |
| 6,981,628 B2 | | 1/2006 | Wales | |

(Continued)

FOREIGN PATENT DOCUMENTS
EP    0 592 243 A2    4/1994

(Continued)

OTHER PUBLICATIONS

European Search Report for EP 12153793.0-2310 date of completion is Apr. 13, 2012 (6 pages).

*Primary Examiner* — Brian D Nash

(57) ABSTRACT

A surgical stapler is provided and comprises a handle assembly, an elongated body, an articulable tool assembly, and an articulation mechanism. The articulation mechanism has: a main shaft member connected to an articulation linkage; a retainer having an opening for receiving a shaft portion of the main shaft member; a cam lock having cam locking surfaces and a locking tab; a locking cover defining recesses for receiving the locking tab; an articulation handle having cam surfaces configured to engage the cam locking surfaces of the cam lock.

9 Claims, 17 Drawing Sheets

U.S. PATENT DOCUMENTS

| | | | |
|---|---|---|---|
| 7,143,924 B2 | 12/2006 | Scirica et al. | |
| 7,303,107 B2 | 12/2007 | Milliman et al. | |
| 7,328,828 B2 | 2/2008 | Ortiz et al. | |
| 7,419,080 B2 | 9/2008 | Smith et al. | |
| 7,431,188 B1 | 10/2008 | Marczyk | |
| 7,434,716 B2 | 10/2008 | Viola | |
| 7,455,208 B2 | 11/2008 | Wales et al. | |
| 7,481,348 B2 | 1/2009 | Marczyk | |
| 7,588,177 B2 | 9/2009 | Racenet et al. | |
| 7,624,902 B2 * | 12/2009 | Marczyk et al. | 227/175.1 |
| 7,640,830 B2 | 1/2010 | Bonis | |
| 7,654,431 B2 | 2/2010 | Hueil et al. | |
| 7,670,334 B2 | 3/2010 | Hueil et al. | |
| 7,690,547 B2 | 4/2010 | Racenet et al. | |
| 7,694,865 B2 | 4/2010 | Scirica | |
| 7,703,653 B2 | 4/2010 | Shah et al. | |
| 7,753,904 B2 | 7/2010 | Shelton, IV et al. | |
| 7,780,054 B2 | 8/2010 | Wales | |
| 7,780,055 B2 | 8/2010 | Scirica et al. | |
| 7,784,662 B2 | 8/2010 | Wales et al. | |
| 7,793,814 B2 | 9/2010 | Racenet et al. | |
| 7,815,091 B2 | 10/2010 | Marczyk | |
| 7,819,896 B2 | 10/2010 | Racenet | |
| 7,861,906 B2 | 1/2011 | Doll et al. | |
| 7,870,810 B2 | 1/2011 | Da Dalt et al. | |
| 7,909,220 B2 | 3/2011 | Viola | |
| 7,918,230 B2 | 4/2011 | Whitman et al. | |
| 2005/0006434 A1 | 1/2005 | Wales et al. | |
| 2005/0184124 A1 * | 8/2005 | Scirica et al. | 227/176.1 |
| 2006/0094931 A1 | 5/2006 | Danitz et al. | |
| 2008/0061108 A1 * | 3/2008 | Scirica | 227/175.1 |
| 2008/0083807 A1 | 4/2008 | Beardsley et al. | |
| 2008/0141744 A1 | 6/2008 | Desaphie et al. | |
| 2008/0179375 A1 * | 7/2008 | Scirica | 227/176.1 |
| 2009/0039137 A1 | 2/2009 | Viola | |
| 2009/0088792 A1 | 4/2009 | Hoell, Jr. et al. | |
| 2009/0114699 A1 | 5/2009 | Viola | |
| 2009/0206130 A1 * | 8/2009 | Hall et al. | 227/175.2 |
| 2010/0163596 A1 | 7/2010 | Marczyk | |
| 2010/0163597 A1 | 7/2010 | Shah et al. | |
| 2010/0237130 A1 | 9/2010 | Scirica | |
| 2010/0320253 A1 | 12/2010 | Marczyk | |

FOREIGN PATENT DOCUMENTS

| | | |
|---|---|---|
| WO | WO 2005/037329 A2 | 4/2005 |

* cited by examiner

LOCKING ARTICULATION MECHANISM FOR SURGICAL STAPLER

BACKGROUND

1. Technical Field

The present disclosure relates to surgical instruments having one or more articulation portions. More particularly, the present disclosure relates to a mechanism for locking the articulating portion of the surgical instrument in a plurality of positions.

2. Background of Related Art

Various instruments have been modified for use in closed procedures, i.e., laparoscopic, arthroscopic, endoscopic. Such instruments typically include an elongated body portion configure to extend through an opening in a patient, i.e., through an access port, and/or thorough a natural orifice, e.g., anus, mouth.

Many of these instruments adapted for closed procedures include an articulable tool assembly mounted on a distal end of an elongated body portion. The tool assembly is controlled remotely from the handle assembly mounted on the proximal end of the elongated body portion. An articulation mechanism mounted on the handle assembly allows for the remote articulation of the tool assembly relative to the elongated body portion. Generally, the articulation mechanism includes a lever mounted on the handle assembly that, when turned, advances or retracts an articulation linkage. The articulation link extends through the elongated body portion and is operably connected to the tool assembly. Longitudinal advancement and retraction of the articulation linkage and causes articulation of the tool assembly. The tool assembly is maintained in a desired position solely through the friction between the lever and the handle. In this manner, if a clinician were to accidentally contact the tool assembly with a structure within the body with sufficient force, the force could cause the tool assembly to be deflected from the desired position.

Therefore, it would be beneficial to have an articulation mechanism configured to selectively lock the tool assembly in one or more position.

SUMMARY

Accordingly, a surgical instrument including a locking displacement mechanism is provided.

DESCRIPTION OF THE DRAWINGS

Embodiments of a locking articulation mechanism are disclosed herein with reference to the drawings, wherein.

DETAILED DESCRIPTION

Embodiments of the presently disclosed locking articulation mechanism will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user. Although the articulation mechanism of the present disclosure will be described as relates to a surgical stapling device, the presently disclosed articulation mechanism may be modified for use with other surgical devices.

Figure 1:
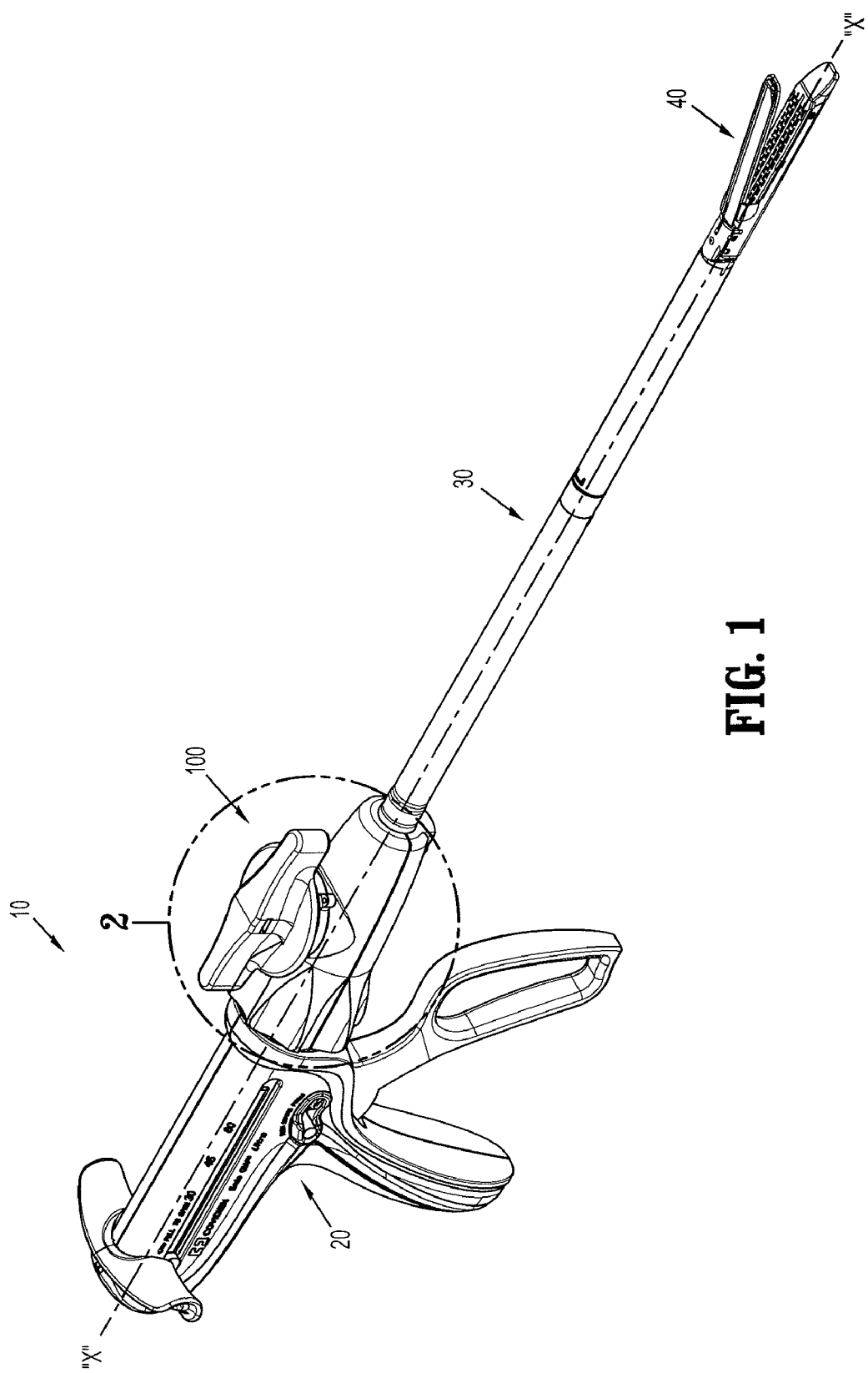
FIG. 1 is a perspective view of a surgical stapler including a locking articulation mechanism according to an embodiment of the present disclosure.

FIGS. 1-22 illustrate an embodiment of a locking articulation mechanism according to the present disclosure, shown generally as locking articulation mechanism 100. As shown in FIG. 1, and as will be discussed hereinbelow, locking articulation mechanism 100 is incorporated into a surgical stapler 10. Surgical stapler 10 includes a handle assembly 20, an elongated body 30 extending from handle assembly 20 and a tool assembly 40 mounted on a distal end of elongated body 30. The structure and function of surgical stapler 10 will only be described herein to the extent necessary to fully disclose locking articulation mechanism 100. For a more detailed description of the structure and function of a surgical stapler similar to surgical stapler 10, please refer to commonly owed U.S. Pat. No. 5,865,361 to Milliman et al., the content of which is incorporated herein in by reference in its entirety.

Figure 2:
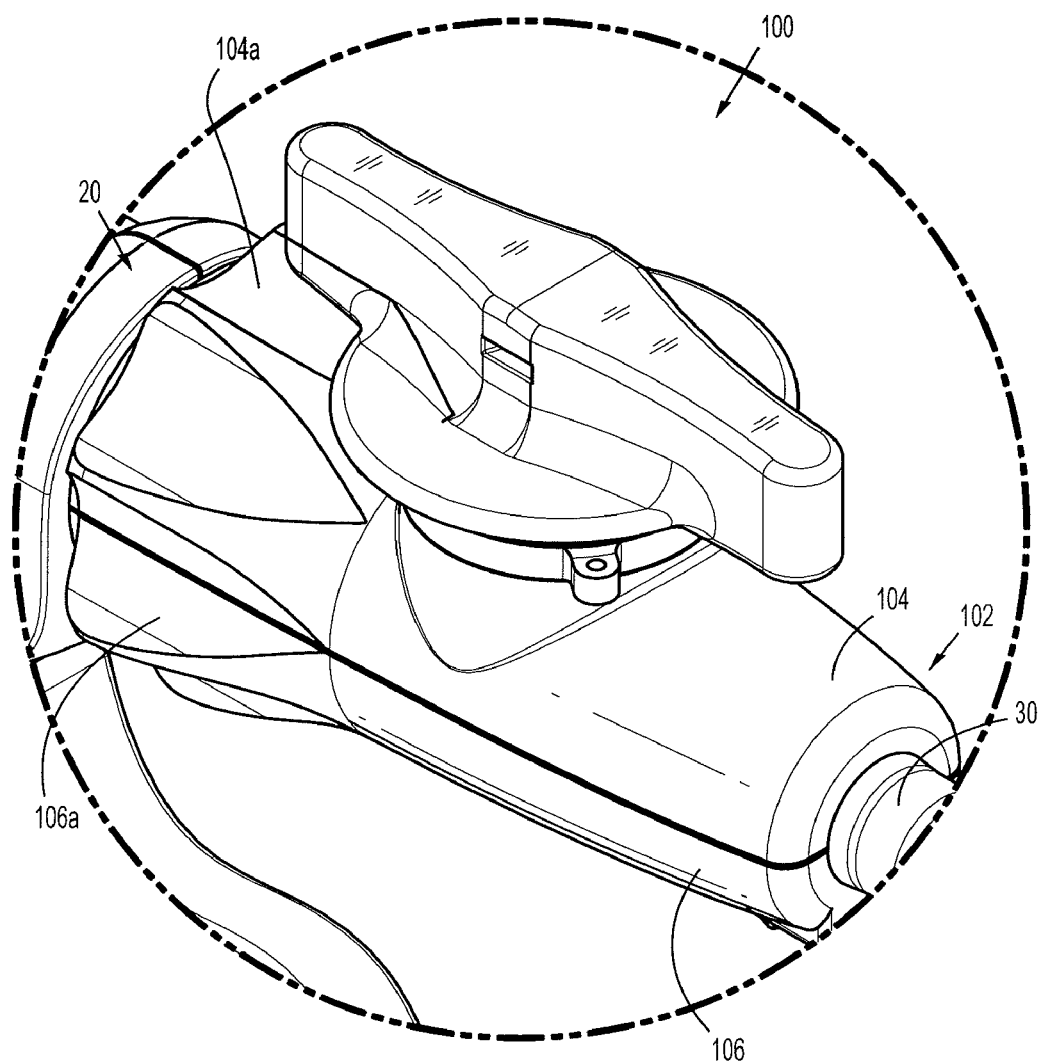
FIG. 2 is an enlarged perspective view of portion 2 of FIG. 1.
Figure 3:
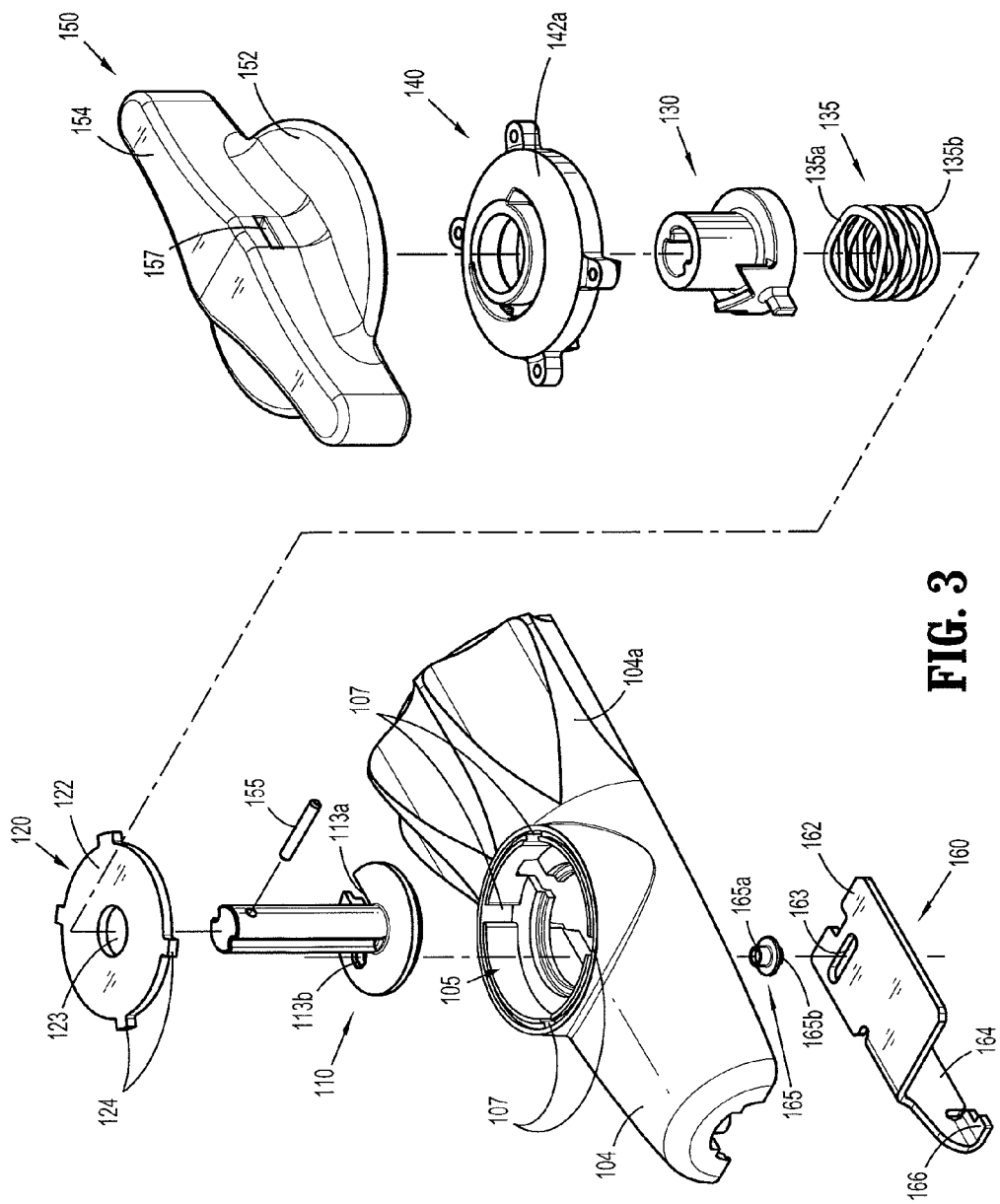
FIG. 3 is an exploded perspective view of the locking articulation mechanism of FIG. 1.

With reference now to FIGS. 1-3, articulation mechanism 100 includes an articulation housing 102 having upper and lower housing or knob halves 104, 106. Upper and lower housing halves 104, 106 are configured to be received about a distal end of handle assembly 20 and a proximal end of elongated body 30. Articulation housing 102 is configured to facilitate rotation of elongated body 30 about a longitudinal axis "x" (FIG. 1). Each of upper and lower housing halves 104, 106 include knurled proximal ends 104a, 106a configured for operable engagement by user. Upper housing half 104 defines an opening 105 (FIG. 3) extending therethrough. Upper housing half 104 further defines a plurality of slots 107 extending radially outwardly of opening 105. As shown, upper housing half 104 includes four (4) slots 107, however, upper housing half 104 may define more or fewer than four slots 107.

Figure 4:
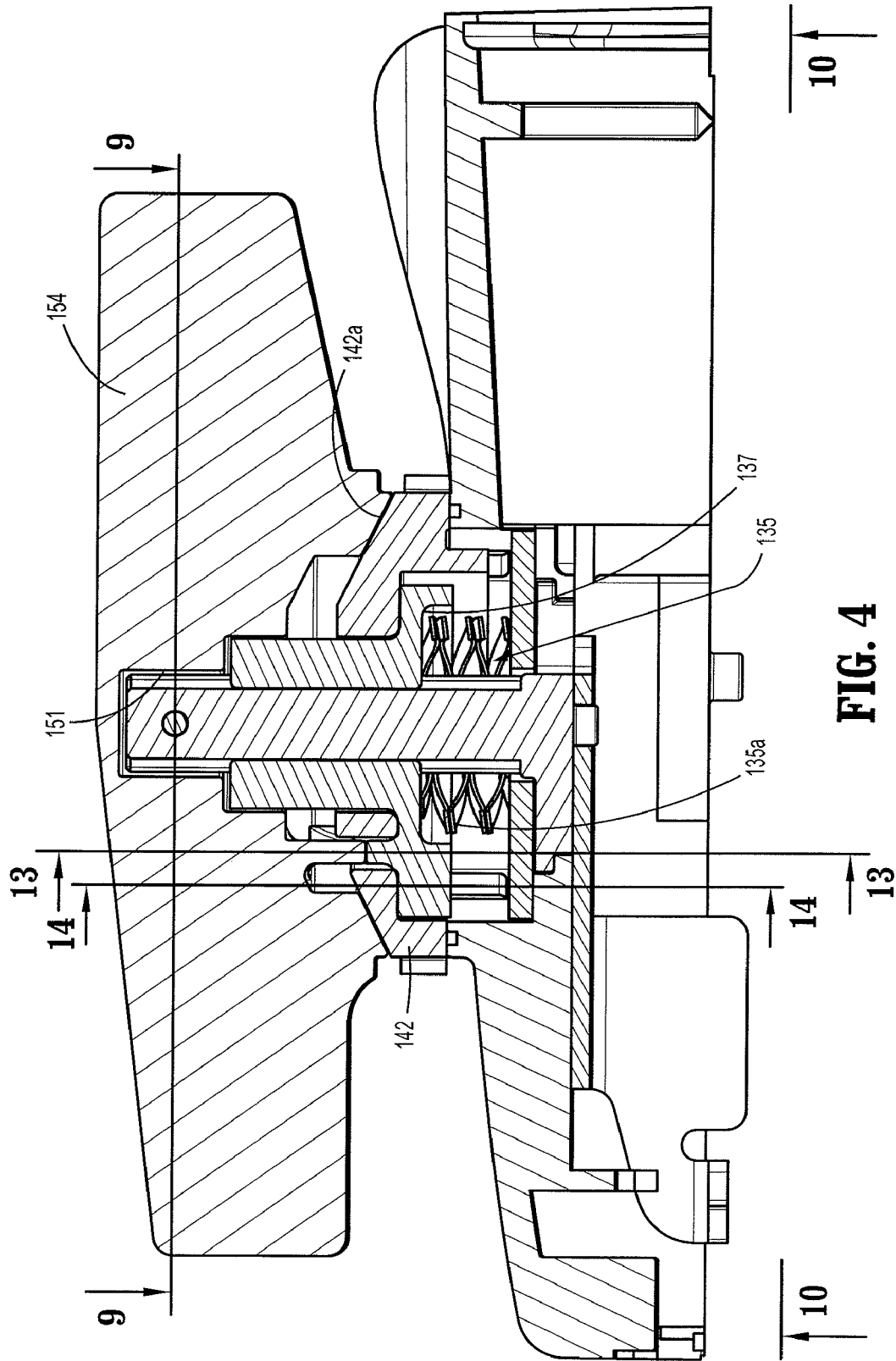
FIG. 4 is a cross-sectional side view of the locking articulation mechanism of FIG. 1.

With reference now to FIGS. 3 and 4, articulation mechanism 100 further includes a main shaft member 110, a retainer 120 a cam lock 130, a locking cover 140, an articulation lever 150 and a channel yoke 160. As discussed above, the term "proximal" refers to that part or component closer to the user or operator. Since the user will engage articulation lever 150 of articulation mechanism 100, as shown in FIGS. 3 and 4, reference will be made to articulation lever 150 being at a proximal end of locking articulation mechanism 100, while channel yoke 160 is located at a distal end thereof.

Figure 5:
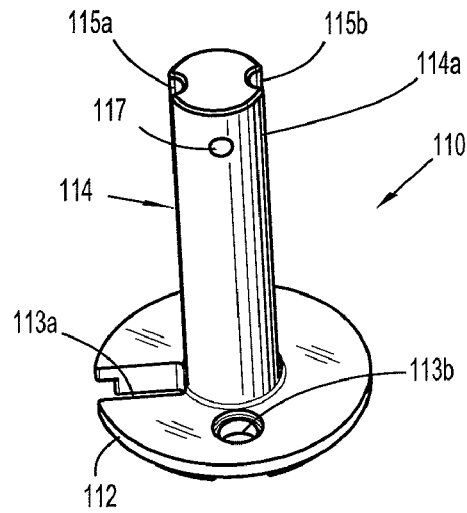
FIG. 5 is a perspective view of a main shaft of the locking articulation mechanism of FIG. 1.

Still referring to FIGS. 3, 4 and 5, main shaft member 110 includes a base portion 112 and a shaft portion 114 extending from base portion 112. Base portion 112 is configured to be rotatably received within opening 105 of upper housing half 104. Base portion 112 includes a radially outward extending slot 113a. Slot 113a The sensor cap (barrel shaped part) strokes axially and contains a protrusion feature that engages and disengages the slot in the radial portion of the main shaft. The purpose of slot 113a will be discussed below. Base portion 112 further includes a cam member. More specifically, an opening 113b is formed therethrough and is configured to engage a proximally extending portion of 165a of a cam pin 165 (FIG. 3) (As will be discussed in further detail below). Shaft portion 114 of main shaft member 110 includes a pair of longitudinally extending notches 115a, 115b. Notches 115a, 115b form opposed substantially U-shaped recesses that extend the length of shaft portion 114. Although shown having the same U-shape profile, recesses 115a, 115b may include alternatively shaped profiles and/or the profiles may differ in shape. Shaft portion 114 further includes an opening 117 extending radially through a proximal end 114a thereof. As will be discussed in further detail below, opening 117 is configured to receive a pin 155 (FIG. 3) to secure articulation handle or lever 150 with main shaft 110.

With continued reference to FIGS. 3 and 4, retainer 120 forms a substantially planar disk 122. Disk 122 includes a plurality of radially outwardly extending tabs 124. As shown, disk 122 includes four (4) tabs 124 corresponding in number and placement to slots 107 formed about opening 105 in upper housing half 104. The number and spacing of tabs 124 may vary to depending on the number and placement of slots 107 formed in upper housing half 104. It is contemplated that disk 122 may include fewer tabs 124 than slots 107. Retainer 120 further includes an opening 123 extending through the center of disk 122. Opening 123 is sized to receive shaft portion 114 of main shaft member 110.

Figure 6:
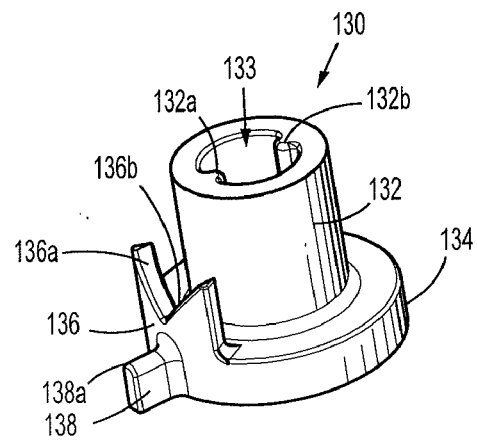
FIG. 6 is a perspective view of a cam lock of the locking articulation mechanism of FIG. 1.

With reference now to FIGS. 3, 4 and 6 cam lock 130 includes a substantially annular body 132 and a flange portion 134. Annular body 132 defines a longitudinal bore 133 extending therethrough configured to receive shaft portion 114 of main shaft member 110. Annular body 132 includes a pair of ridges 132a, 132b extending the length of bore 133. Ridges 132a, 132b correspond to notches 115a, 115b formed on shaft portion 114 of main shaft 110. A cam member 136 is formed on flange portion 134 of cam lock 130. Cam member 136 is radially spaced from annular body 132 and extends proximally from flange portion 134. Cam member includes cam locking surfaces 136a, 136b. A locking tab 138 extends radially outward from cam member 136. Locking tab 138 includes a rounded proximal surface 138a. Flange portion 134 defines a recess 137 (FIG. 4) in a distal surface thereof configured to receive a proximal end 135a of a biasing member 135. As will be discussed in further detail below, biasing member 135 is configured to be received about shaft portion 114 of main shaft 110 between retainer 120 and cam lock 130. As shown, biasing member 135 includes a wave spring, however, biasing member 135 may include any apparatus capable of selectively biasing cam lock 130 away from retainer 120. Wave springs include a low profile, thereby minimizing the space required between cam lock 130 and retainer 120 for receiving biasing member 135.

Figure 7:
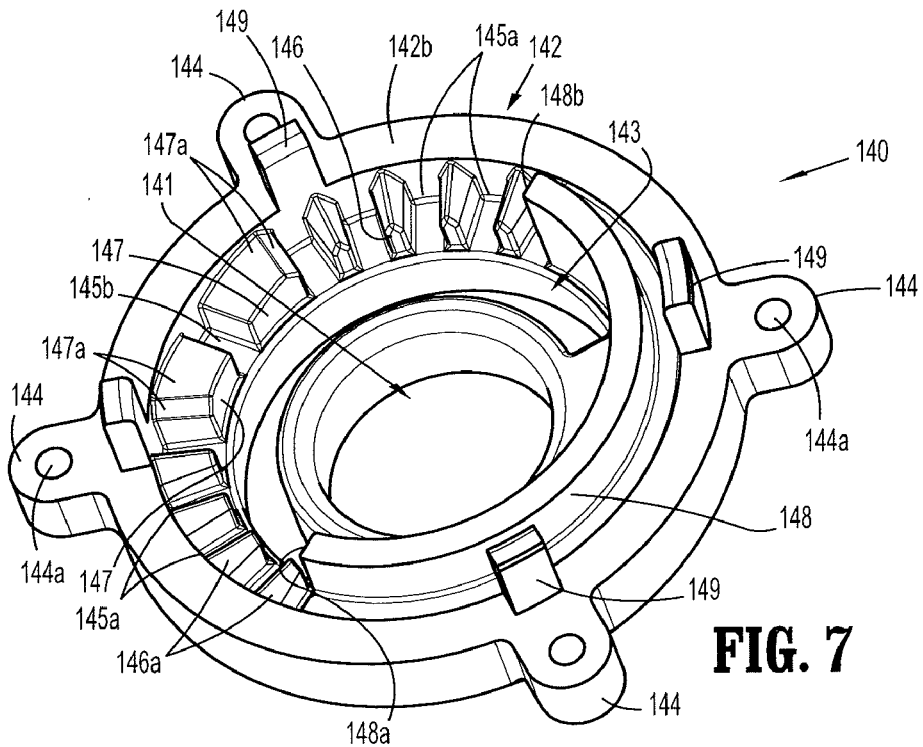
FIG. 7 is a perspective view of the distal surface of a locking cover of the locking articulation mechanism of FIG. 1.
Figure 8:
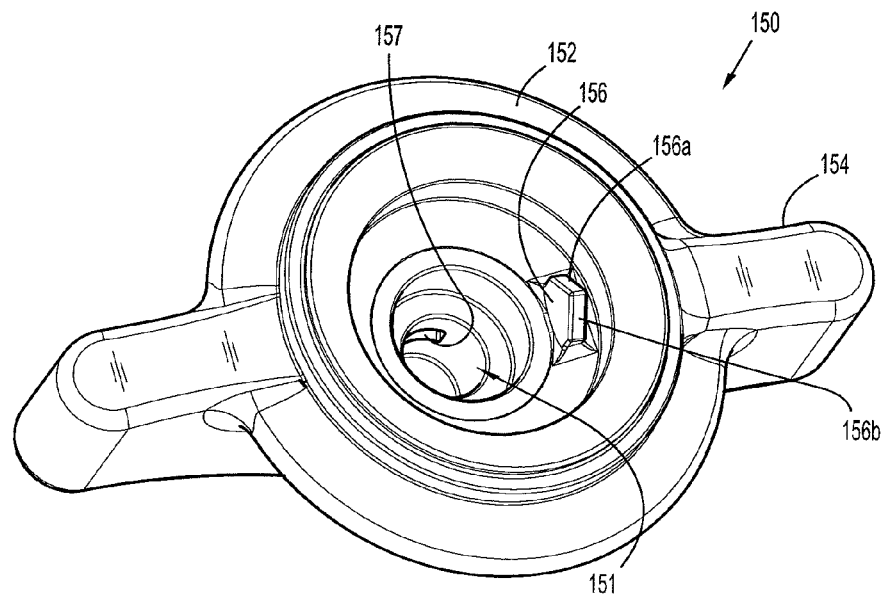
FIG. 8 is a perspective view of the distal surface of the articulation lever of the locking articulation mechanism of FIG. 1.

With reference now to FIGS. 3, 4 and 7, locking cover 140 defines a substantially annular member 142 having a proximal surface 142a and a distal surface 142b (FIG. 7). Proximal surface 142a is configured to engage and stabilize articulation handle or lever 150. As shown, proximal surface 142a is inclined, however, other configurations may be employed for stabilizing articulation lever 150. A plurality of flanges 144 extend radially outward from annular member 142 for securing locking cover 140 to upper housing half 104 of articulation housing 102. Other methods for attaching the cover can be used, such as ultrasonic welding, detents, bayonet lock, adhesives, etc. As shown, locking cover 140 includes four (4) flanges 144 evenly spaced about annular member 142. Locking cover 140 may include more or less than four flanges 144 and flanges 144 may or may not be evenly spaced about annular member 142. As shown, each flange 144 defines an aperture 144a configured to receive a screw or other fastening device. Alternatively, flanges 144 may include locking tabs or be otherwise configured to securely engage upper housing half 104 of articulation housing 102.

With particular reference to FIG. 7, annular member 142 defines a longitudinal bore 141 extending therethrough and a semi-circular cut-out 143 radially spaced from longitudinal bore 141. As will be discussed in further detail below, cut-out 143 is configured to slidingly receive cam member 136 of cam lock 130. Distal surface 142b of annular member 142 includes a plurality of recesses 145a extending radially outward from semi-circular cut-out 143 along first and second ends thereof. A central recess 145b is formed at the midpoint of semi-circular cut-out 143. Each of recesses 145a and 145b are configured to receive locking tab 138 of cam lock 130. As will be discussed in further detail below, central recess 145b corresponds to a position in which when locking tab 138 is received therein, tool assembly 40 is in a non-articulated position. Recess 145b is defined by a pair of dividers 147 having chamfered surfaces 147a. Recesses 145a are defined by dividers 146 having chamfered surfaces 146a. Dividers 146 may be of similar size, as shown, to provide recesses 145a of similar spacing. In this manner, tool assembly 40 may be articulated in even increments. Alternatively, dividers 146 may be of differing sizes, thereby resulting in unequal incremental articulation of tool assembly 40. As will be discussed in further detail below, chamfered surfaces 146a, 147b of dividers 146, 147, respectively, are configured to direct locking tab 138 of cam lock 130 within one of recesses 145a, 145b.

With reference still to FIG. 7, a semi-circular extension 148 extends distally from annular member 142. First and second ends 148a, 148b of extension 148 are configured to interact with cam lock 130 to prevent over-rotation of articulation mechanism 100. A plurality of feet 149 extend distally from distal surface 142b of annular member 142. Feet 149 correspond in number and location to slots 107 formed about opening 105 in upper housing half 104 (FIG. 3). Feet 149 are configured to be received within slots 107 of upper housing half 104 and engage tabs 124 of retainer 120.

Figure 9:
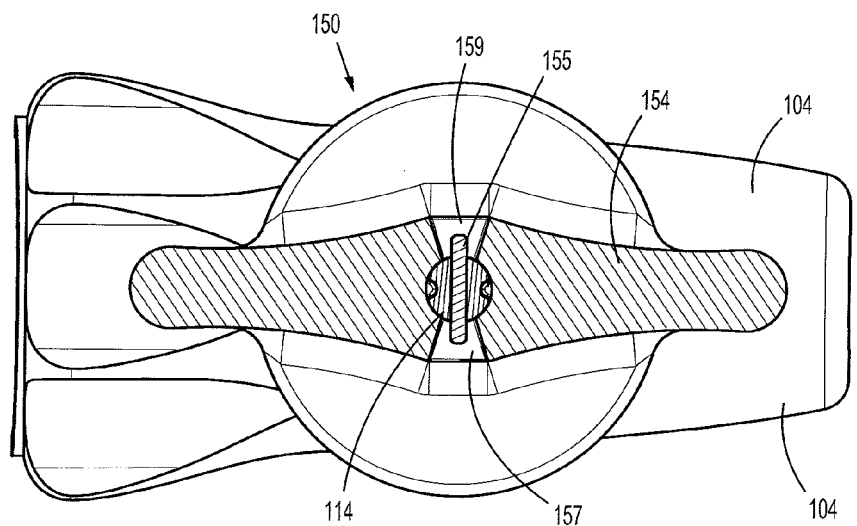
FIG. 9 is a cross-sectional top view of the locking articulation mechanism of FIG. 1 taken along line 9-9 of FIG. 4.

With reference now to FIGS. 3, 4, 8 and 9, articulation handle or lever 150 includes a circular base 152 and an elongated engagement portion 154. Articulation lever 150 defines a recess 151 configured to receive a proximal end 114a of shaft portion 114 of main shaft 110 and be received about annular body 132 of cam lock 130. Articulation lever 150 further includes a cam member 156 extending distally from within recess 151. Cam member 156 includes cam surfaces 156a, 156b. As will be discussed in further detail below, cam surfaces 156a, 156b are configured to engage cam locking surfaces 136a, 136b formed on cam member 136 of cam lock 130. With particular reference to FIG. 9, articulation lever 150 further defines a pair of horizontal cut-outs 157, 159 extending radially outward from recess 151 through elongated engagement portion 154. Cut-outs 157, 159 are positioned for alignment with opening 117 formed on proximal end 114a of shaft portion 114 of main shaft 110. As will be discussed in further detail below, cut-outs 157, 159 are configured to permit partial rotation of articulation lever 150 relative to main shaft 110 prior to engagement of articulation lever 150 with locking pin 155.

With reference now to FIGS. 3 and 4, channel yoke 160 is a substantially L-shaped bracket having a horizontal portion 162 and a vertical portion 164. Extending from vertical member 164 is a flange 166. Flange 166 is configured to engage an articulation linkage (not shown), which, as discussed above, is operably connect to tool assembly 40. Horizontal member 162 defines a slot 163 configured to receive a distally extending portion 165b of cam pin 165.

The articulation mechanism can be configured to be included on a surgical instrument, such as a surgical stapler. The articulation mechanism may interact with a sensor mechanism of the surgical stapler. The surgical stapler includes a structure extending through the elongate shaft of the stapler. The structure, which may include a tubular member, is displaced proximally upon the engagement of an articulating surgical stapling loading unit with the elongate shaft. Loading units that do not articulate are configured not to displace the tubular member. A sensor cap is arranged with the proximal end of the tubular member so as to be displaced along with the tubular member. The sensor cap has a protrusion that is received in the slot 113a to prevent movement of the main shaft 110 unless and until the sensor cap is displaced. In this way, the articulation mechanism cannot be moved unless an articulating loading unit is engaged with the elongate shaft of the surgical stapler. The slot 113a is utilized to lock the articulation mechanism when a loading unit is not loaded, to unlock the articulation mechanism when an articulating loading unit is loaded, and lock the articulation mechanism when a non-articulating loading unit is loaded. U.S. Pat. No. 5,865,361 to Milliman et al. discloses a sensor tube of a sensor mechanism that interacts with articulating loading units.

The assembly of articulation mechanism 100 will now be described with reference to FIGS. 3-12. Referring initially to FIGS. 1-3, prior to attaching upper and lower housing halves 104, 106 to elongated body 30 of surgical stapler 10, channel yoke 160 is positioned within handle assembly 20. Channel yoke 160 is positioned such that flange 166 formed on vertical member 164 of channel yoke 160 engages an articulation link (not shown) extending from within elongated body 30. As discussed above, longitudinal translation of the articulation link causes articulation of tool assembly 40. Upper and lower housing halves 104, 106 are then fit together about a proximal end of elongated body 30 and a proximal end of handle assembly 20. Upper and lower housing halves 104, 106 may be joined with a snap fit connection, mechanical fasteners, bonding, adhesive or any other suitable method.

Figure 10:
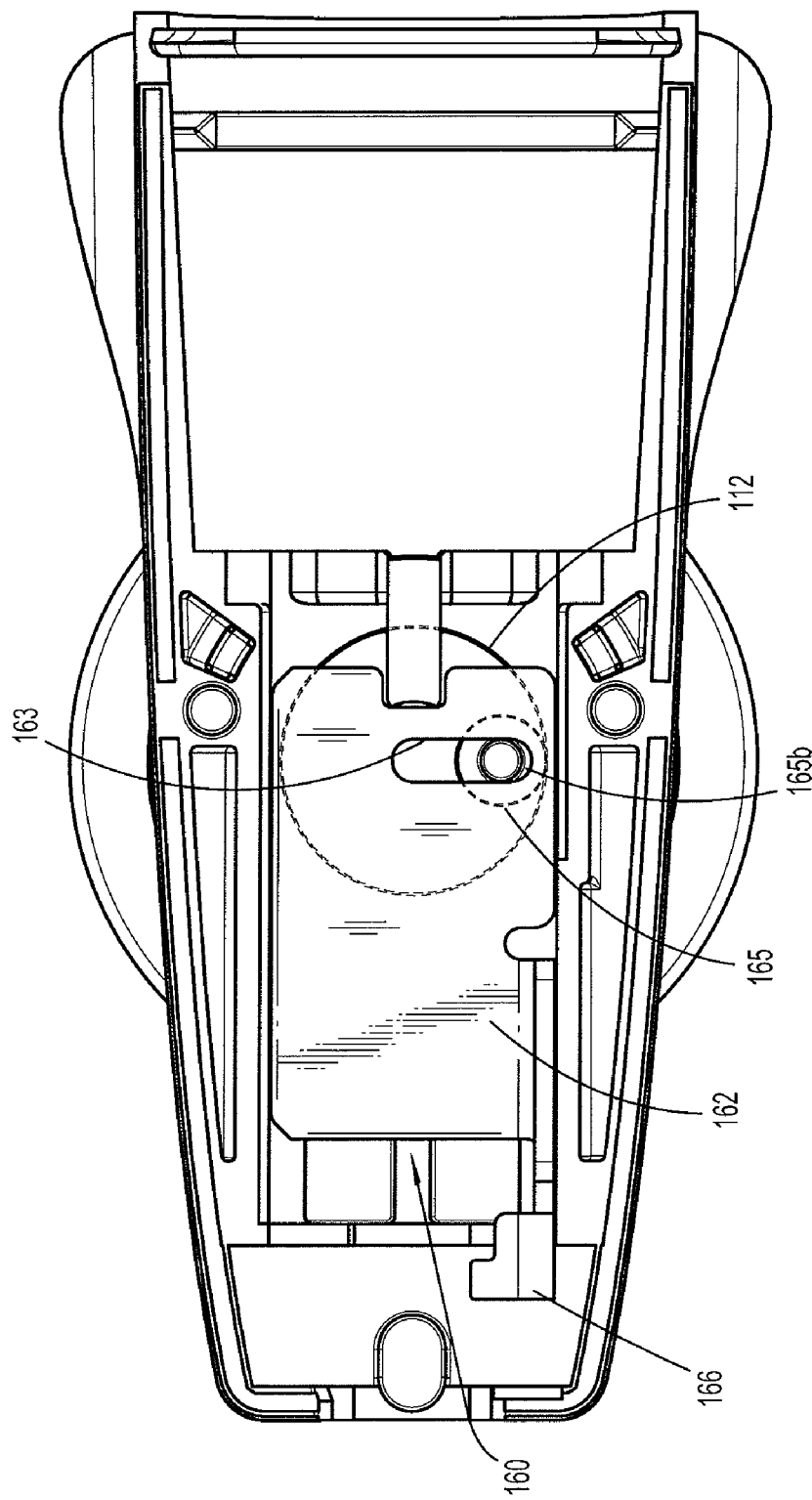
FIG. 10 is a bottom view of the locking articulation mechanism of FIG. 1 taken along line 10-10 of FIG. 4.

With reference now to FIGS. 3, 4 and 10, cam pin 165 is next secured to base portion 112 of main shaft 110. Proximal portion 165a of cam pin 165 is received through opening 113b in base portion 112. In one embodiment, once proximal portion 165a of cam pin 165 is received through opening 113b, proximal portion 165a is peened to secured cam pin 165 to main shaft 110. Alternatively, mechanical fasteners or other suitable methods may used to secure cam pin 165 to main shaft 110. Once cam pin 165 is secured within opening 112b of in base portion 112, main shaft 110 is positioned within opening 105 of upper housing half 104 such that distal portion 165b of cam pin 165 is received within slot 163 formed in horizontal member 162 of channel yoke 160.

With continued reference to FIGS. 3 and 4, retainer 120 is next placed over and about shaft portion 114 of main shaft 110 and positioned such that tabs 124 extending radially outward from disk 122 thereof are received within slots 107 formed about opening 105 of upper housing half 104. Biasing member 135 is next received about shaft portion 114 of main shaft 110 such that a distal end 135b of biasing member 135 engages disk 122 of retainer 120. Cam lock 130 is then received about shaft portion 114. As discussed above, annular body 132 of cam lock 130 includes a pair of opposed ridges 132a, 132b extending the length of longitudinal bore 133. Ridges 132a, 132b correspond with notches 115a, 115b formed in shaft portion 114 of main shaft 110. Engagement of ridges 132a, 132b of cam lock 130 with respective notches 115a, 115b of main shaft 110 assures proper alignment of cam lock 130 with main shaft 110 and further keys cam lock 130 with main shaft 110. In this manner, rotation of main shaft 110 causes corresponding rotation of cam lock 130.

Figure 11:
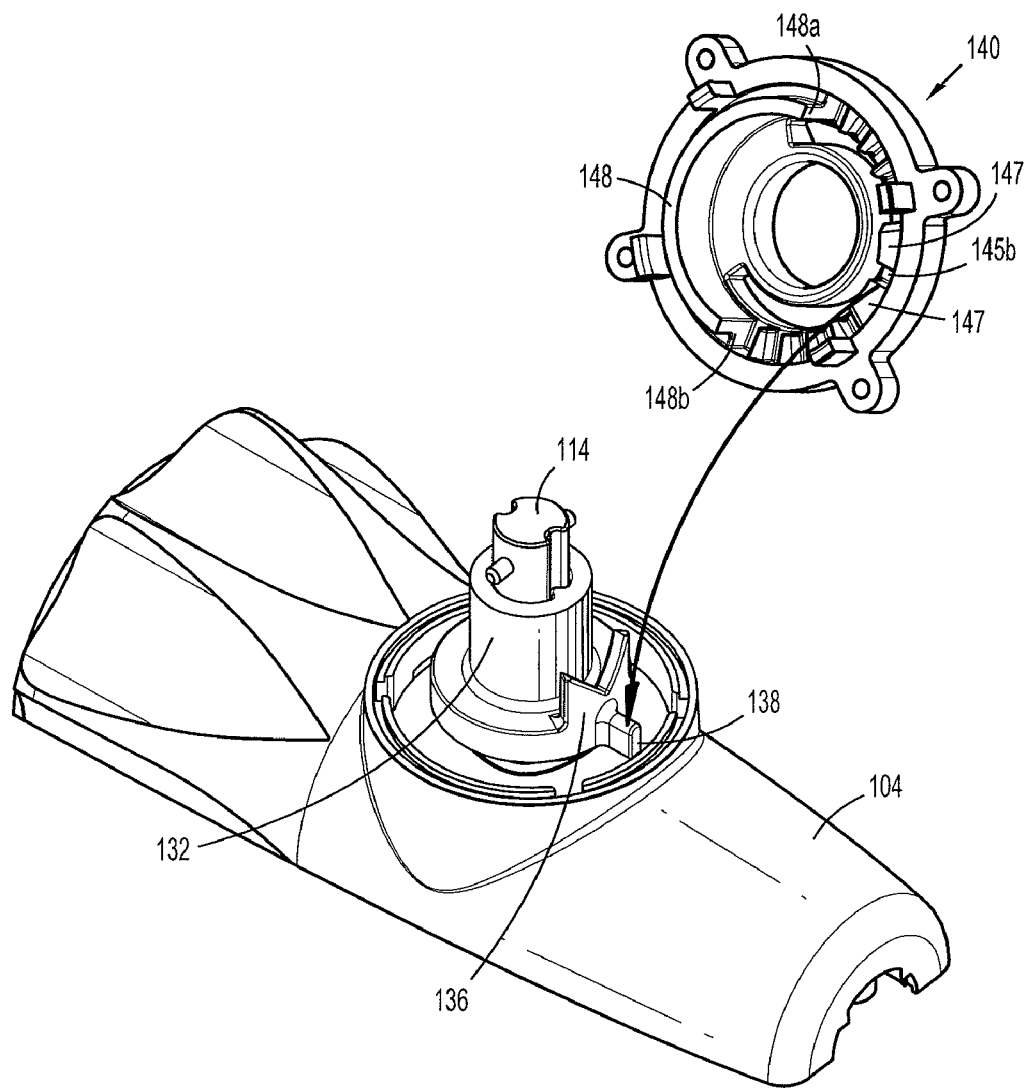
FIG. 11 is a perspective view of the locking cover of FIG. 7 separated from the locking articulation mechanism of FIG. 1.
Figure 12:
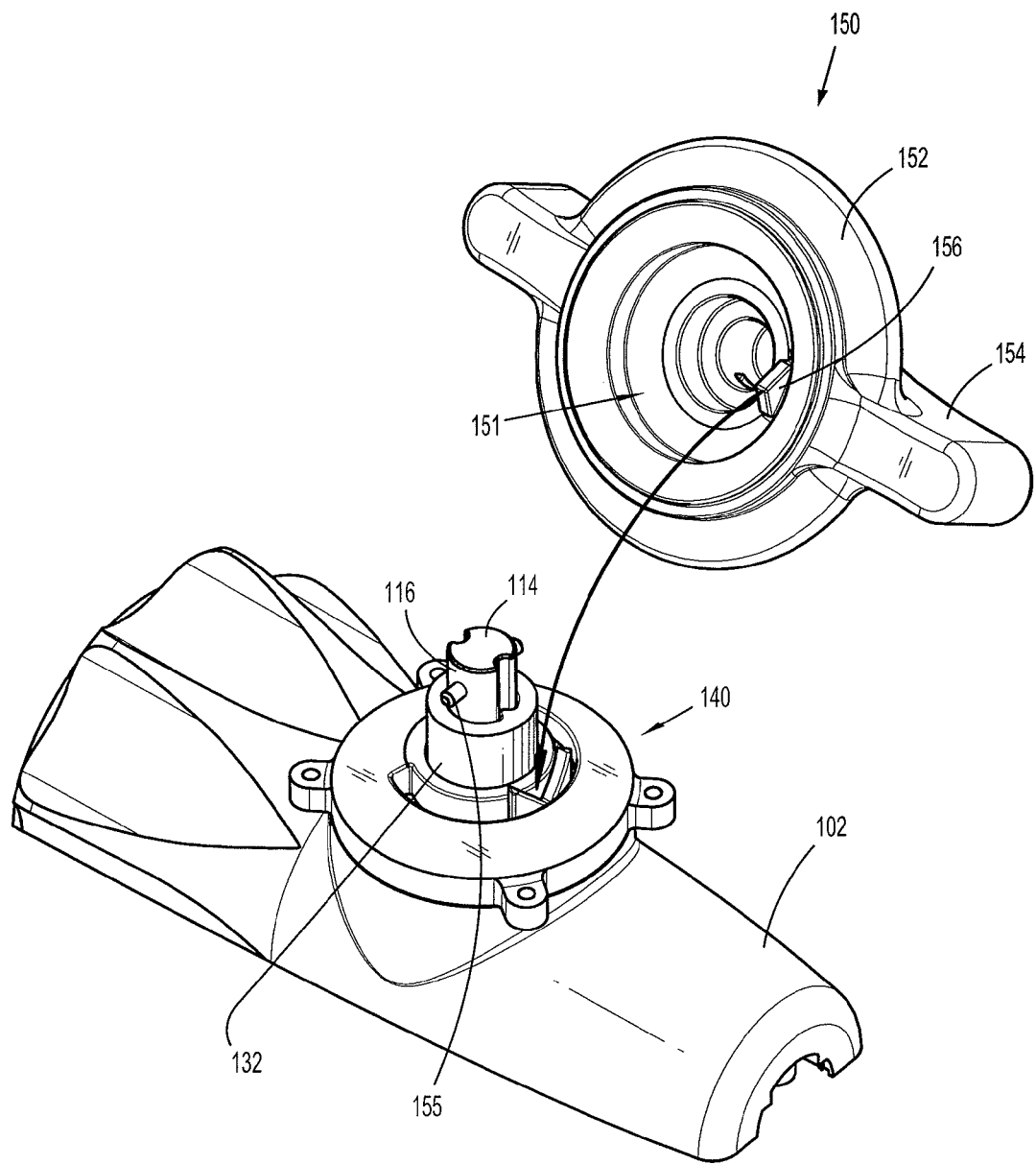
FIG. 12 is a perspective view of the articulation lever of FIG. 8 separated from the locking articulation mechanism of FIG. 1.

With reference now to FIGS. 3, 4 and 11, locking cover 140 is then received about shaft portion 114 of main shaft 110 and over annular body 132 of cam lock 130 such that cam member 136 of cam lock 130 is received through semi-circular cut-out 143. As seen in FIG. 11, upon initial engagement of lock cover 140 with cam lock 130, biasing member 135 biases cam lock 130 towards locking cover 140 such that locking tab 138 of cam lock 130 is received within recess 145b formed between dividers 147. Locking cover 140 is secured to upper housing half 104 as discussed above.

With reference to FIGS. 3, 4, 9 and 12, articulation lever 150 is next placed on proximal end 114a of shaft 114 such that cam member 156 formed on base 152 of articulation lever 150 engages cam member 136 of cam lock 130 and opening 117 formed in proximal end 114a of shaft 114 aligns with horizontal cut-outs 157, 159 formed in engagement portion 154 of articulation lever 150. Locking pin 155 is then inserted through opening 117 formed in shaft portion 114 of main shaft 110 to secure articulation handle or lever 150 to main shaft 110. As seen in FIG. 9, locking pin 155 is configured to extend completely through shaft portion 114 of main shaft 110 and into each of horizontal cut-outs 157, 159. Locking pin 155 may be secured within opening 117 by friction fit, adhesive or other suitable method.

Figure 13:
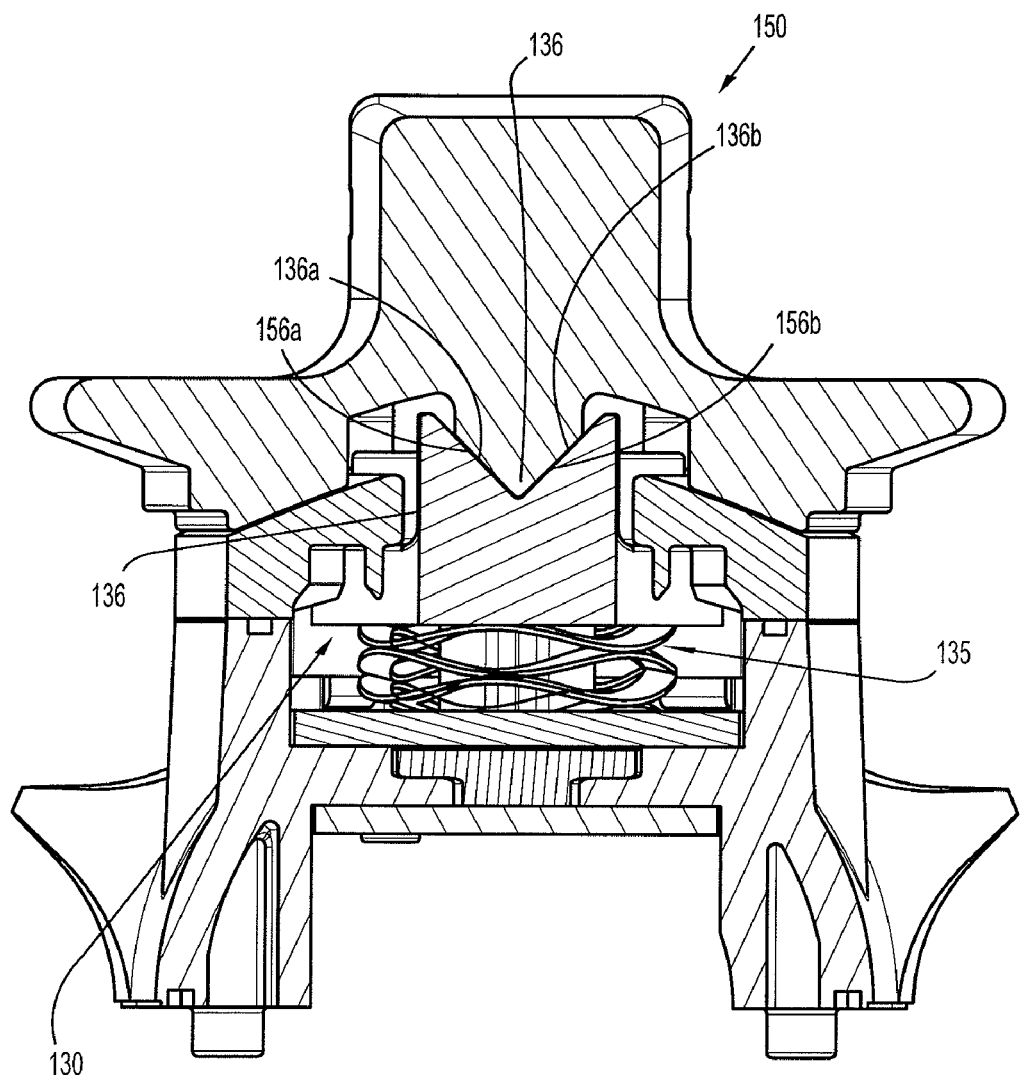
FIG. 13 is a cross-sectional end view of the locking articulation mechanism of FIG. 1 taken along line 13-13 of FIG. 4.
Figure 14:
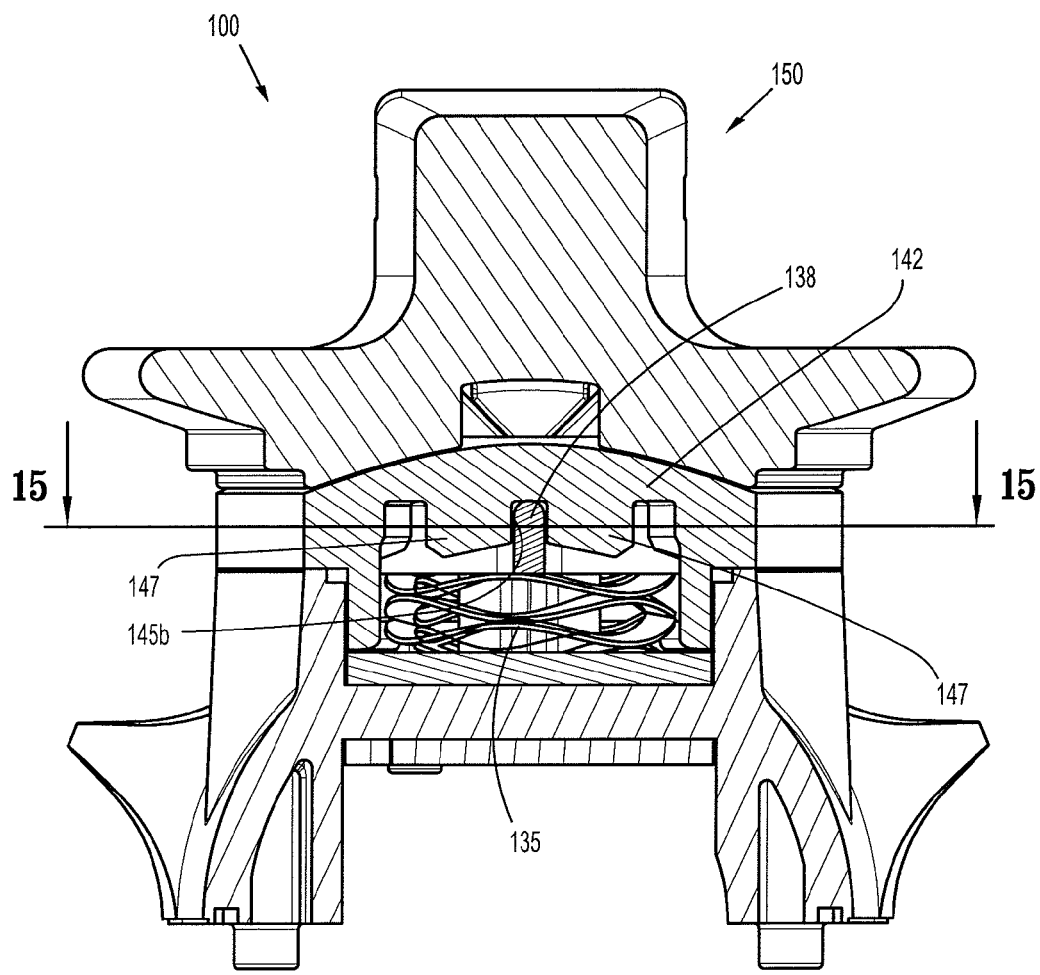
FIG. 14 is a cross-sectional end view of the locking articulation mechanism of FIG. 1 taken along line 14-14 of FIG. 4.
Figure 15:
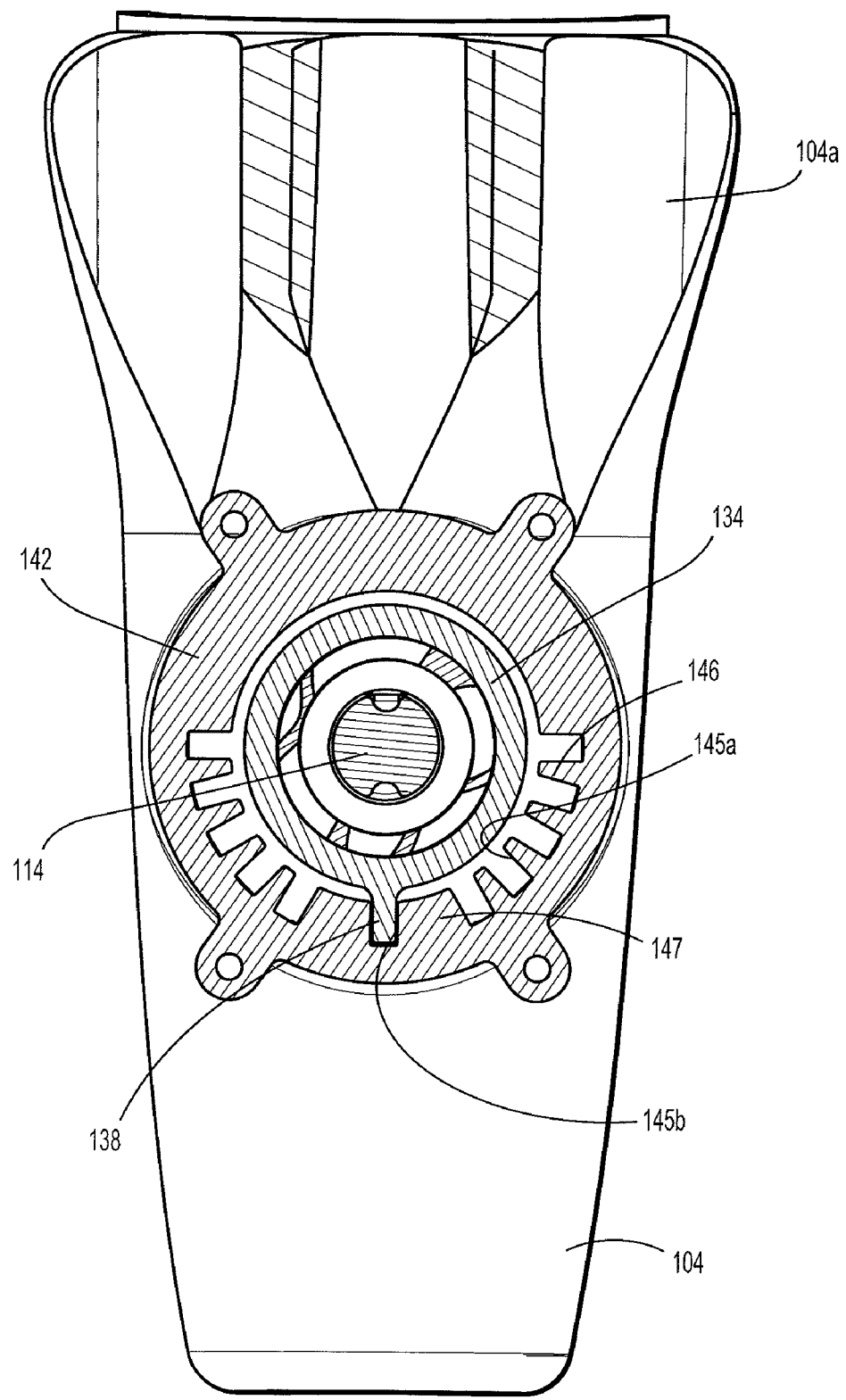
FIG. 15 is a cross-sectional top view of the locking articulation mechanism of FIG. 1 taken along line 15-15 of FIG. 14.

The use of articulation mechanism 100 will now be described with reference to figures. Referring initially to FIGS. 1, 4, 9 and 13-15, articulation mechanism 100 is shown in an initial position. When articulation mechanism 100 is in the initial position, elongated body 30 and tool assembly 40 of surgical stapler 10 are in a non-articulated or straight configuration. With particular reference to FIG. 13, in the initial position, cam surfaces 136a, 136b formed on cam member 136 of cam lock 130 are aligned with cam surfaces 156a, 156b formed on cam member 156 of articulation lever 150. Biasing member 135 biases cam surfaces 136a, 136b of cam lock 130 into engagement with cam surfaces 156a, 156b of articulation lever 150. This engagement provides a positive lock that does not rely on friction. With particular reference now to FIGS. 14 and 15, in the initial position, locking tab 138 formed on flange 134 of cam lock 130 is received within recess 145b formed between dividers 147 of lock cover 140. The chamfered surfaces 146 on the dividers that define the central recess 145b are relatively large chamfers that tend to return the mechanism to the unarticulated position, whereas the relatively smaller chamfers on the other dividers lock the articulation mechanism in articulated positions. These chamfers may be configured to minimize the torque required to move between articulated positions. Referring briefly to FIG. 9, in the initial position, locking pin 155 is centered within horizontal cut-outs 157, 159 formed in engagement portion 154 of articulation lever 150.

Figure 16:
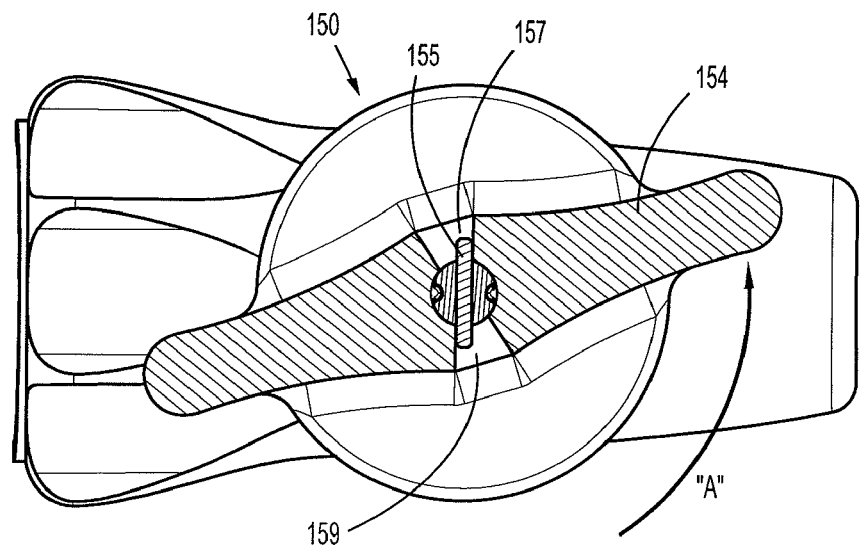
FIG. 16 is the cross-sectional top view of FIG. 9, wherein the articulation lever is in a second position.
Figure 17:
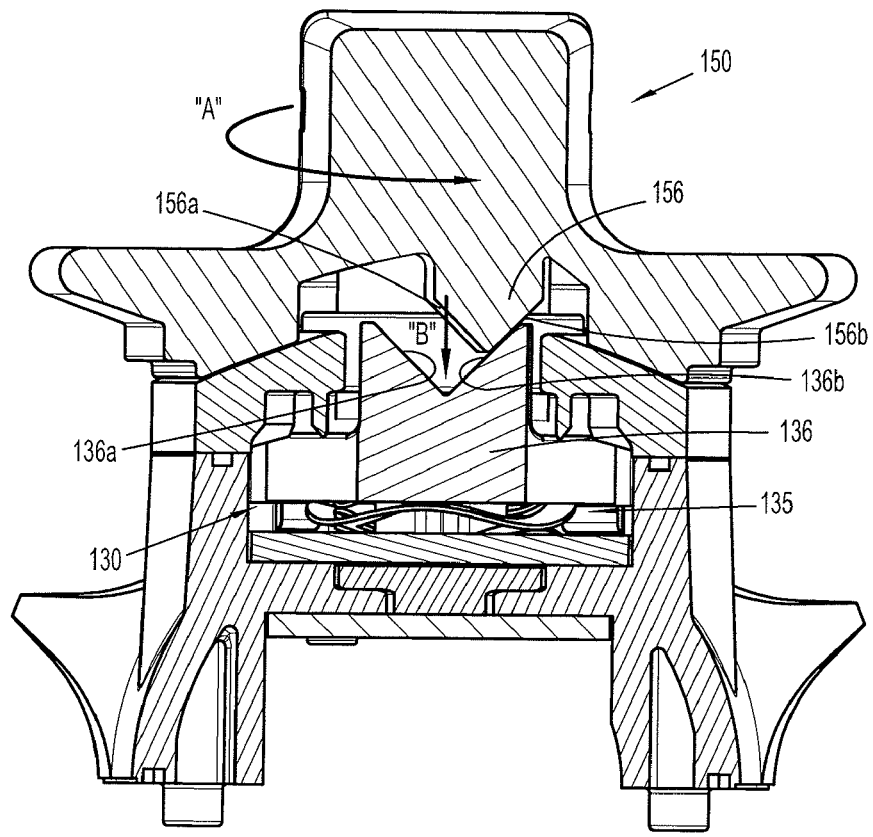
FIG. 17 is the cross-sectional end view of FIG. 13, wherein the articulation lever is in the second position.
Figure 18:
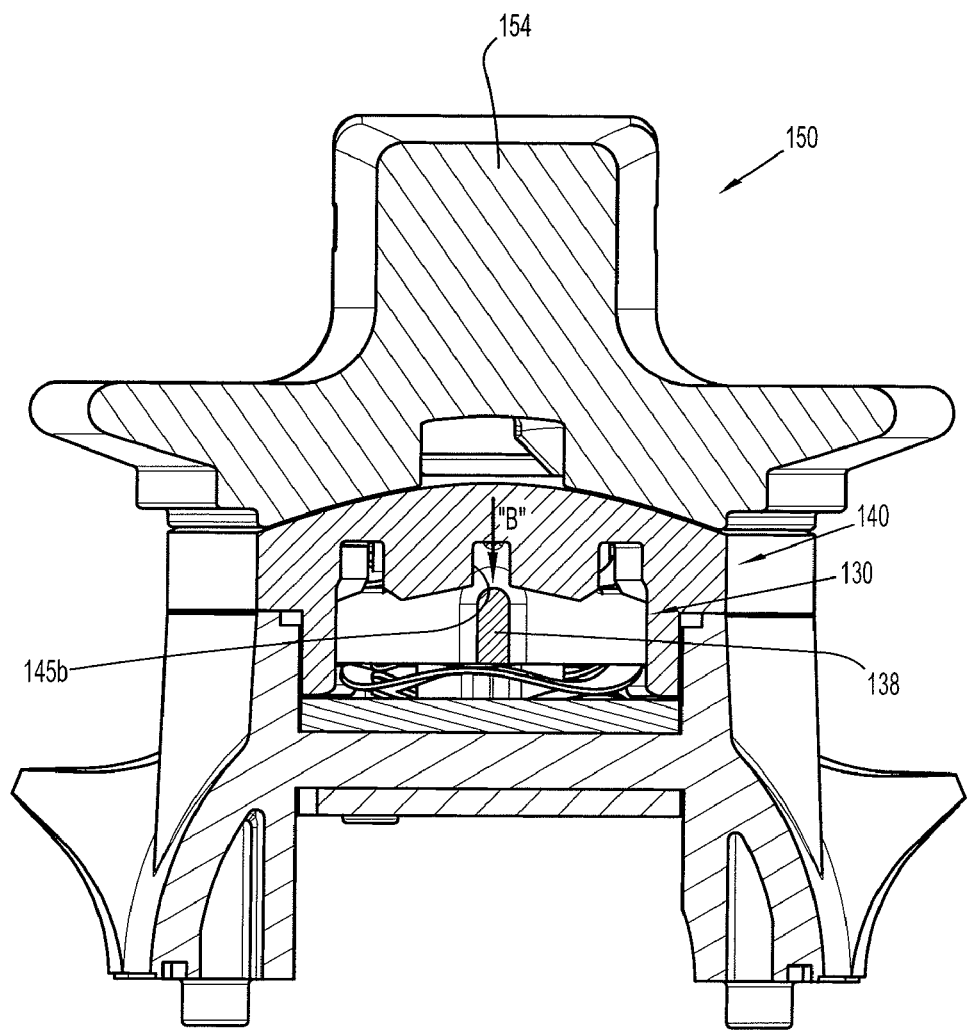
FIG. 18 is the cross-sectional end view of FIG. 14, wherein the articulation lever is in the second position.
Figure 19:
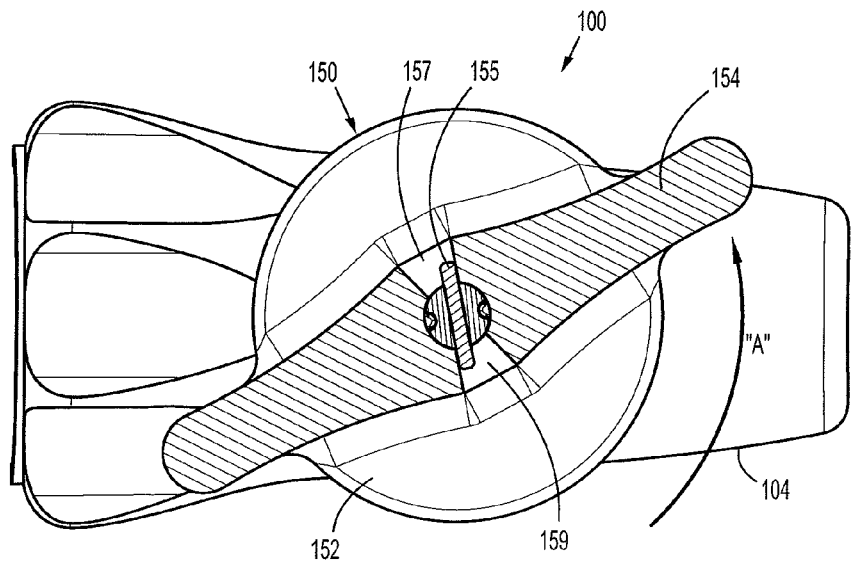
FIG. 19 is the cross-section top view of FIGS. 9 and 16, wherein the articulation lever is third position.

With reference now to FIGS. 16-18, during use, articulation lever 150 is rotated in a first, counter-clockwise direction, as indicated by arrow "A". Although the following discussion refers to rotating articulation lever 150 in a first, counter-clockwise direction to cause the articulation of tool assembly 40 in a first direction, articulation lever 150 may also be rotated in a second, clockwise direction to cause the articulation of tool assembly 40 in a second direction. As seen in FIG. 16, the configuration of horizontal cut-outs 157, 159 formed in engagement portion 154 allows articulation lever 150 to be rotated relative to shaft portion 114 of main shaft 110 from the initial position (FIG. 9) to a second position (FIG. 16) without causing the rotation of main shaft 110. Turning to FIG. 17, rotation of articulation lever 150 from the initial position to the second position rotates articulation lever 150 relative to cam lock 130. Rotation of articulation lever 150 relative to cam lock 130 causes movement of cam member 156 of articulation lever 150 relative to cam member 136 of locking member 130. As seen in FIG. 17, rotation of articulation lever 150 in a first direction, causes engagement of cam surfaces 156b of cam member 156 with cam surface 136b. Engagement of cam surface 156b with cam surface 136b forces cam lock 130 distally away from articulation lever 150, as indicated by arrow "B". Movement of cam lock 130 results in compression of biasing member 135. With reference to FIG. 18, distal movement of cam lock 130 further causes disengagement of locking tab 138 from within recess 145b of locking cover 140.

Figure 20:
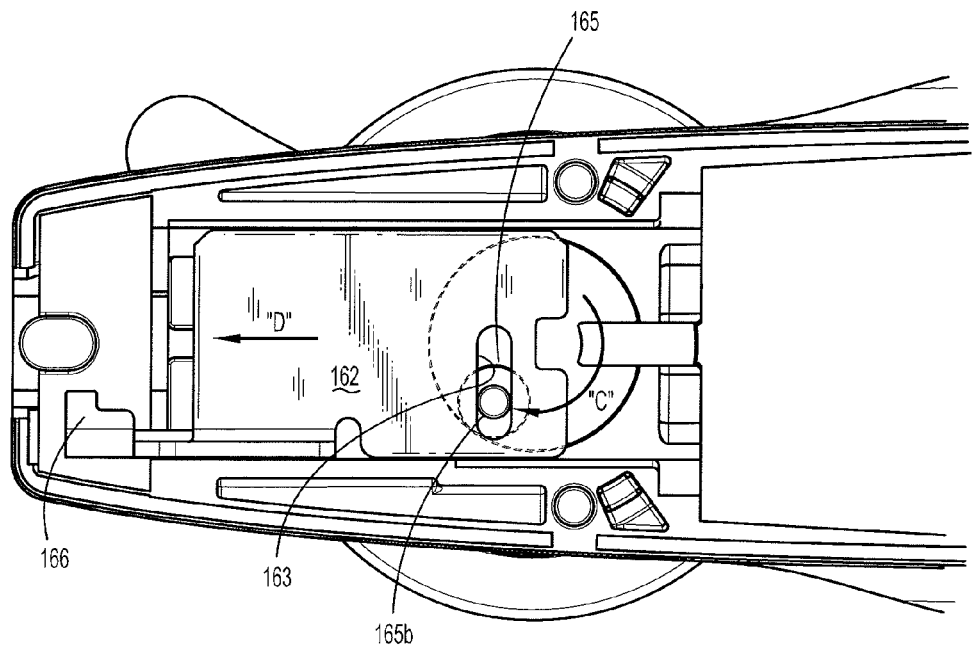
FIG. 20 is a bottom view of the locking articulation mechanism of FIG. 1, wherein the articulation lever is in the third position.
Figure 21:
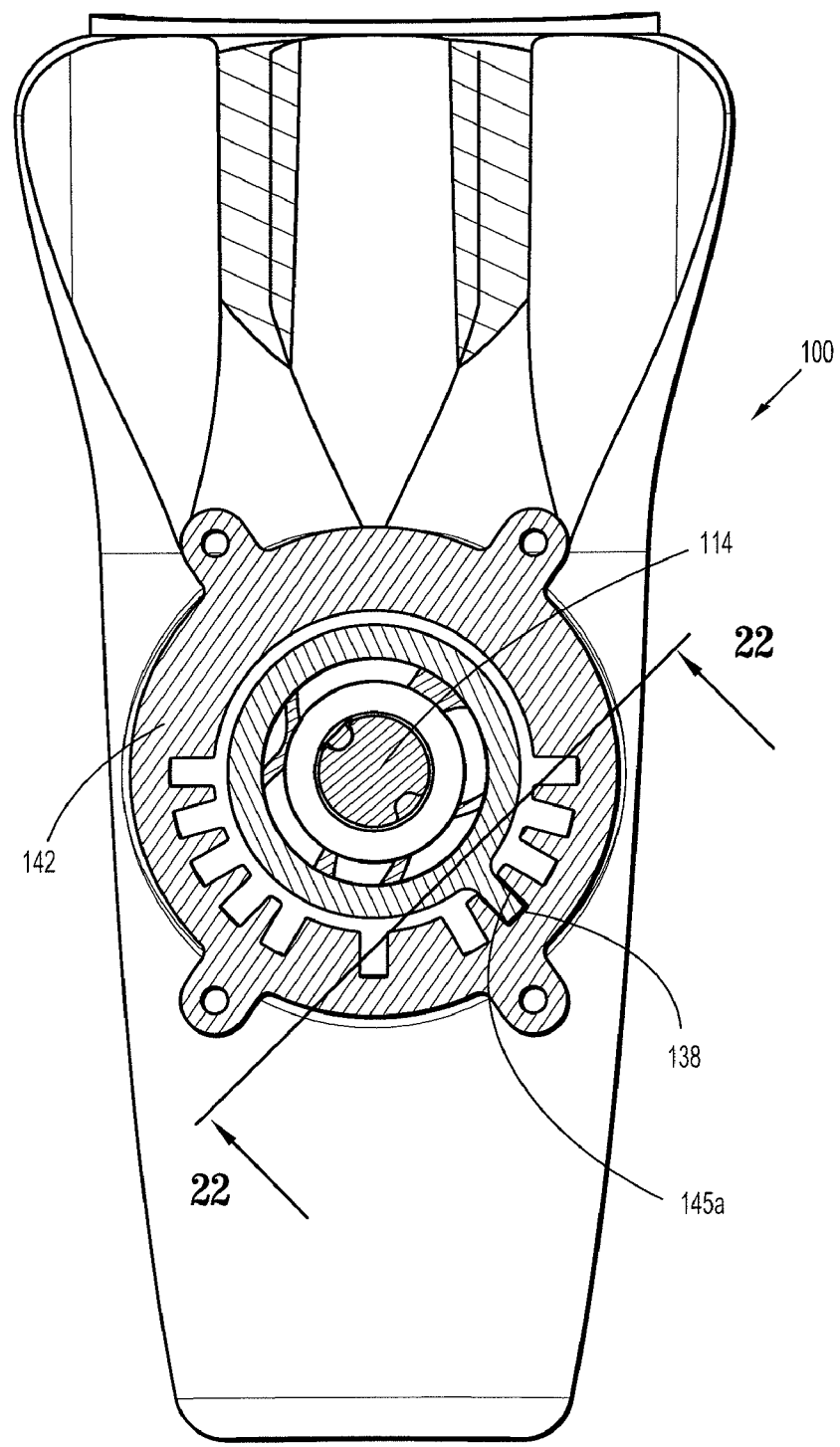
FIG. 21 is the cross-section top view of FIG. 15, wherein the articulation mechanism is locked position.

With reference now to FIGS. 19-22, engagement of locking pin 155 with engagement portion 154 of articulation lever 150 keys main shaft 110 with articulation lever 150, thereby resulting in any further rotation of articulation lever 150 causing rotation of main shaft 110. Thus, continued rotation of articulation lever 150 in the first direction, as indicated by arrow "A", causes rotation of main shaft 110 in the same first direction, as indicated by arrow "C" (FIG. 20). Rotation of main shaft 110 causes movement of cam member 165 which causes longitudinal translation of channel yoke 160, as indicated by arrow "D". As discussed above, channel yoke 160 is operably connected to an articulation linkage (not shown). Translation of channel yoke 160 causes translation of the articulation linkage which causes articulation of tool assembly 40 (FIG. 1) relative to elongated body 30.

Figure 22:
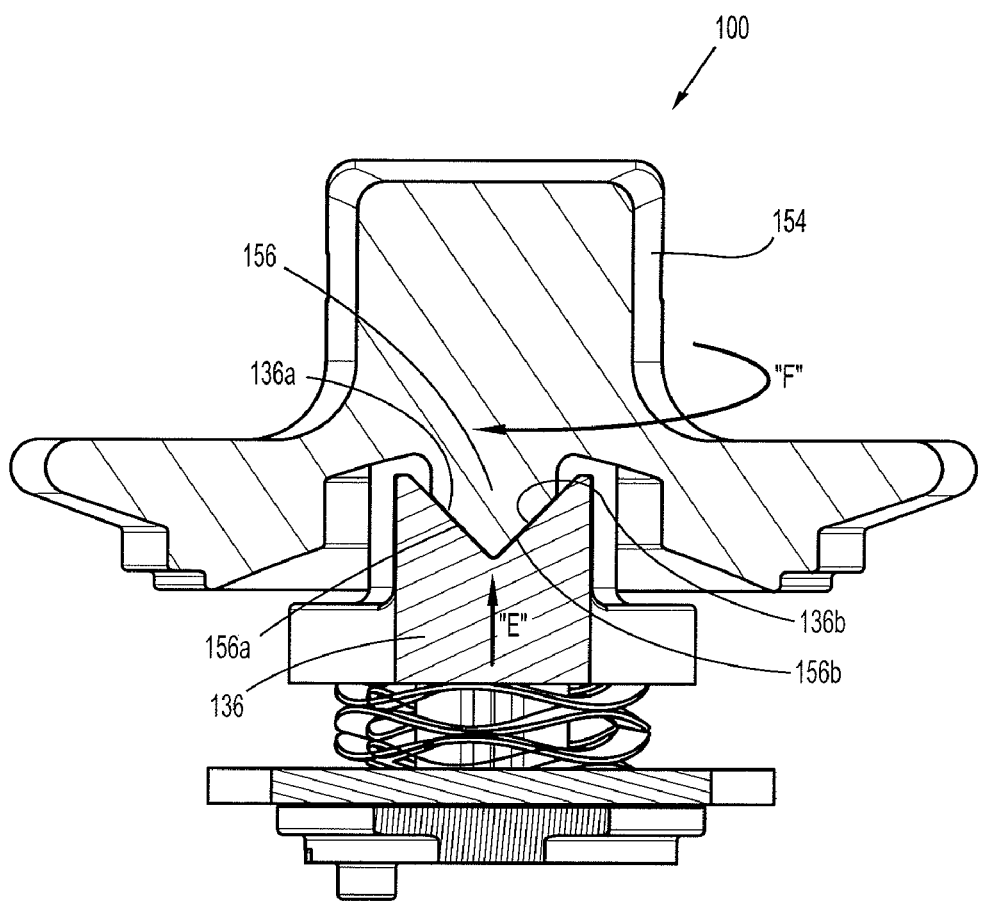
FIG. 22 is a cross-sectional side view of the articulation lever of FIG. 1 taken along lines 22-22 of FIG. 21.

Articulation lever 150 may be rotated in the first direction "A" until locking tab 138 of cam lock 130 engages end surface 148b (FIG. 11) of semi-circular extension 148 of cover lock 140. Once articulation lever 150 has been rotated sufficiently to articulate tool assembly 40 (FIG. 1) to a desired position, the force applied to articulation lever 150 to cause rotation of articulation lever 150 and main shaft 110 is released. When the force applied to articulation lever 150 is released, the force compressing biasing member 135 is also released. The biasing force of biasing member 135 against cam lock 130 urges cam lock 130 proximally towards articulation lever 150, as indicated by arrow "E" (FIG. 22). Movement of cam lock 130 towards articulation lever 150 causes rotation of articulation lever 150 in a second direction, as indicated by arrow "F", as cam surfaces 136a, 156a, 136b, 156b of cam members 136, 156, respectively, reengage. Proximal movement of cam lock 130 relative to articulation lever 150 further causes locking tab 138 of cam lock 130 to be received within one of recesses 145a of lock cover 140. Rounded surface 138a of locking tab 138 and chamfered surfaces 146a of dividers 146 facilitate reception of locking tab 138 within one of recesses 145a. The chamfered surfaces 146a also provide a tactile "clicking" feedback.

Once locking tab 138 is received within one of recess 145a, tool assembly 40 is locking in an articulated position and surgical stapler 10 is ready for use. Following use of surgical stapler 10, locking articulation mechanism 100 may be used to articulate tool assembly 40 to another articulated position, in the manner discussed above, or locking articulation mechanism 100 may be use to return tool assembly 40 to the non-articulated position (FIG. 1).

It will be understood that various modifications may be made to the embodiment disclosed herein. For example, as noted hereinabove, the disclosed articulation locking mechanism may modified to provide incremental degrees of articulation. The degrees of articulation may be varied depending on procedure being performed. Therefore, the above description should not be construed as limiting, but merely as exemplifications of particular embodiments. Those skilled in the art will envision other modifications within the scope and spirit of the claims appended hereto.

The invention claimed is:
1. A surgical stapler comprising:
   a handle assembly;
   an elongated body extending from the handle assembly;
   an articulable tool assembly mounted on a distal end of the elongated body; and
   an articulation mechanism operably connected to the handle assembly and configured to selectively articulate and securely lock the tool assembly in one or more positions, the articulation mechanism having:
      a main shaft member mounted for rotation and connected to an articulation linkage;
      a stationary retainer having an opening for receiving a shaft portion of the main shaft member;
      a cam lock having a bore configured to receive the shaft portion of the main shaft member, the cam lock having cam locking surfaces and a locking tab;
      a biasing member disposed between the retainer and cam lock;
      a locking cover defining recesses for receiving the locking tab, the
      recesses including a central recess positioned to correspond to a nonarticulated position;
      an articulation handle having cam surfaces configured to engage the cam locking surfaces of the cam lock, wherein the engagement of the cam locking surfaces and the cam surfaces moves the cam lock against the bias of the biasing member.

2. The surgical stapler according to claim 1, wherein the recesses are defined by dividers having chamfered surfaces.

3. The surgical stapler according to claim 2, wherein the dividers differ in size.

4. The surgical stapler according to claim 2, wherein the dividers include central dividers defining a central recess and other dividers defining recesses for articulated positions.

5. The surgical stapler according to claim 4, wherein the chamfers on the central dividers are relatively large, and wherein the chamfers on the dividers defining recesses for articulated positions are relatively small.

6. The surgical stapler according to claim 1, wherein the locking cover has a semi-circular extension having ends configured to interact with the cam lock and prevent over-rotation.

7. The surgical stapler according to claim 1, wherein the articulation handle has cutouts that align with an opening formed on the shaft portion, and further comprising a locking pin for securing the articulation handle to the main shaft, the cutouts allowing the articulation handle to pivot before rotating the main shaft.

8. The surgical stapler according to claim 1, wherein a yoke is attached to the main shaft member and the articulation linkage.

9. The surgical stapler according to claim 1, wherein the articulation mechanism further includes a housing configured to receive the retainer therein, the retainer being stationary relative to the housing.

* * * * *